(12) United States Patent
Le

(10) Patent No.: US 10,667,696 B1
(45) Date of Patent: Jun. 2, 2020

(54) ORAL PHOTOGRAPHY SYSTEM

(71) Applicant: Vu Quang Le, Trabuco, CA (US)

(72) Inventor: Vu Quang Le, Trabuco, CA (US)

( * ) Notice: Subject to any disclaimer, the term of this patent is extended or adjusted under 35 U.S.C. 154(b) by 0 days.

(21) Appl. No.: 16/358,147

(22) Filed: Mar. 19, 2019

(51) Int. Cl.
*A61B 5/00* (2006.01)
*A61B 1/06* (2006.01)
*A61B 1/24* (2006.01)
*G03B 15/03* (2006.01)
*G03B 17/56* (2006.01)
*G03B 15/06* (2006.01)

(52) U.S. Cl.
CPC .......... *A61B 5/0088* (2013.01); *A61B 1/0623* (2013.01); *A61B 1/24* (2013.01); *G03B 15/03* (2013.01); *G03B 15/06* (2013.01); *G03B 17/561* (2013.01)

(58) Field of Classification Search
None
See application file for complete search history.

(56) References Cited

U.S. PATENT DOCUMENTS

| 2,560,884 A * | 7/1951 | Nagourney | A61B 5/702 248/124.1 |
| 3,374,342 A * | 3/1968 | Hutchins | G03B 15/03 362/8 |
| 4,392,183 A * | 7/1983 | Ostlund | G03B 15/03 362/11 |
| 7,050,715 B1 * | 5/2006 | Carrington | G03B 15/035 396/182 |
| 2016/0202598 A1 * | 7/2016 | Griffey | G03B 17/561 396/58 |
| 2016/0277660 A1 * | 9/2016 | Kaiser | H04N 5/2252 |
| 2017/0118385 A1 * | 4/2017 | Vargas | A45D 42/10 |

OTHER PUBLICATIONS

Smile Line, Smile Line MDP KIT- #6600-KIT, Mar. 19, 2019, https://smilelineusa.com/product/smile-lite-mdp-full-set-6600-kit/.
Photomed, SDL—Smartphone Dental Light, Mar. 19, 2019, https://www.photomed.net/sdl.htm.

* cited by examiner

*Primary Examiner* — William B Perkey
(74) *Attorney, Agent, or Firm* — John D. Tran; Rhema Law Group

(57) ABSTRACT

An oral photography system and method can include: a chassis, the chassis including a chassis base and a vertical chassis extension, the vertical chassis extension extending upward from the chassis base, the vertical chassis extension including a device clamp having a tightening extension coupled to a top clasp and a bottom clasp, the top clasp and the bottom clasp configured to hold an imaging device perpendicular to the vertical chassis extension, a diffusion panel attachment coupled to the vertical chassis extension, and a light panel attachment coupled to the vertical chassis extension; a diffusion panel releasably affixed to the diffusion panel attachment; and a light panel releasably affixed to the light panel attachment.

20 Claims, 7 Drawing Sheets

ORAL PHOTOGRAPHY SYSTEM

TECHNICAL FIELD

This disclosure relates to photography, more particularly to a system for oral photography.

BACKGROUND

Photographic and video records for use in medical and dental procedures is becoming more important as the ability to capture, store, and analyze these records increases. The single lens reflex camera produces good images but, due to many problems, has failed to provide a useable solution suitable for broad application within the health care industry.

One problem with the single lens reflex camera is the weight. The heft of the camera itself can make it difficult for smaller professionals to maneuver the camera in place and, once there, to maintain stability.

Another problem with the single lens reflex camera is the width of the camera and lens. The width of the camera can make precise angles and tight quarters a challenge.

The size and weight of the single lens reflex camera are only compounded when the camera is used in conjunction with a lighting apparatus. Some lighting apparatuses use a removable diffuser that is either flush with the front surface, resulting in minimal diffusion of light, or a magnetic mount offset diffuser which falls off in real life use.

With the rise in the use and reliance on video in the medicine and dentistry, it is critical that solutions be found to these problems. Solutions have been long sought but prior developments have not taught or suggested any complete solutions, and solutions to these problems have long eluded those skilled in the art. Thus, there remains a considerable need for devices and methods that can reduce weight and width of a photography system for allowing broad application within the health care field.

SUMMARY

An oral photography system and methods, providing significantly reduced weight and width for allowing broad application within the health care field, are disclosed. The oral photography system and methods can include: a chassis, the chassis including a chassis base and a vertical chassis extension, the vertical chassis extension extending upward from the chassis base, the vertical chassis extension including a device clamp having a tightening extension coupled to a top clasp and a bottom clasp, the top clasp and the bottom clasp configured to hold an imaging device perpendicular to the vertical chassis extension, a diffusion panel attachment coupled to the vertical chassis extension, and a light panel attachment coupled to the vertical chassis extension; a diffusion panel releasably affixed to the diffusion panel attachment; and a light panel releasably affixed to the light panel attachment.

Other contemplated embodiments can include objects, features, aspects, and advantages in addition to or in place of those mentioned above. These objects, features, aspects, and advantages of the embodiments will become more apparent from the following detailed description, along with the accompanying drawings.

BRIEF DESCRIPTION OF THE DRAWINGS

The photography system is illustrated in the figures of the accompanying drawings which are meant to be exemplary and not limiting, in which like reference numerals are intended to refer to like components, and in which.

DETAILED DESCRIPTION

Figure 1:
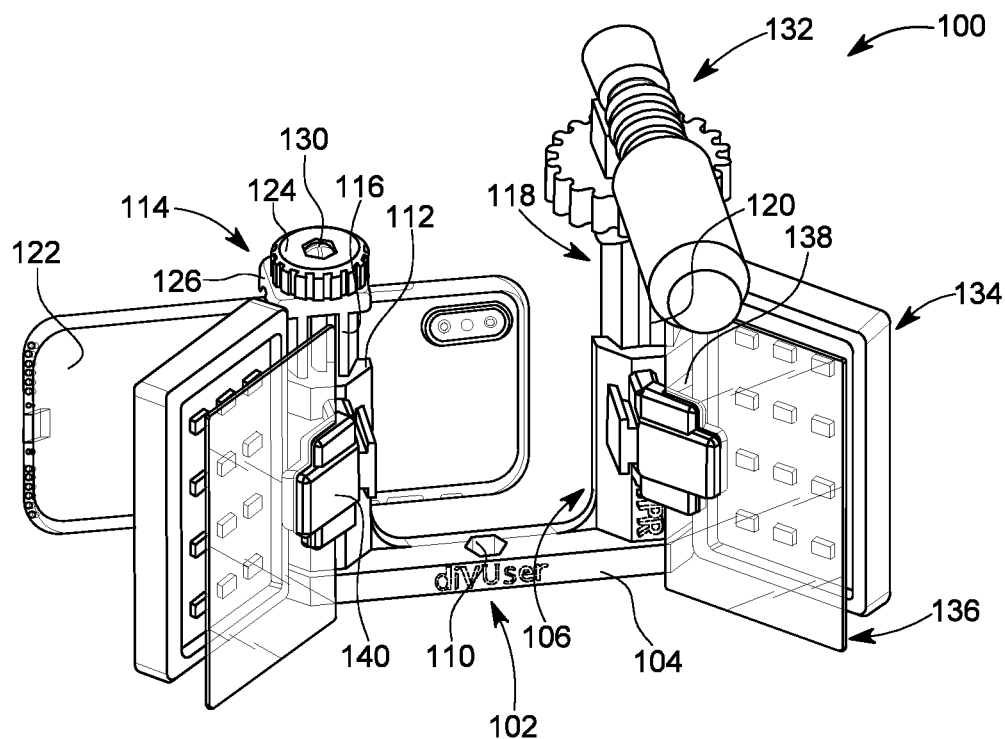
FIG. 1 is a front isometric view of the photography system in a first embodiment.

In the following description, reference is made to the accompanying drawings that form a part hereof, and in which are shown by way of illustration, embodiments in which the photography system may be practiced. It is to be understood that other embodiments may be utilized and structural changes may be made without departing from the scope of the photography system.

When features, aspects, or embodiments of the photography system are described in terms of steps of a process, an operation, a control flow, or a flow chart, it is to be understood that the steps can be combined, performed in a different order, deleted, or include additional steps without departing from the photography system as described herein.

The photography system is described in sufficient detail to enable those skilled in the art to make and use the photography system and provide numerous specific details to give a thorough understanding of the photography system; however, it will be apparent that the photography system may be practiced without these specific details.

In order to avoid obscuring the photography system, some well-known system configurations and descriptions are not disclosed in detail. Likewise, the drawings showing embodiments of the system are semi-diagrammatic and not to scale and, particularly, some of the dimensions are for the clarity of presentation and are shown greatly exaggerated in the drawing FIGs. Generally, the photography system can be operated in any orientation.

As used herein, the term system is defined as a device or method depending on the context in which it is used. For expository purposes, the term "horizontal" as used herein is defined as a plane parallel to the bottom plane or surface of the chassis base, regardless of its orientation. The term "vertical" refers to a direction perpendicular to the horizontal as just defined. Terms, such as "above", "below", "bottom", "top", "side", "higher", "lower", "upper", "over", and "under", are defined with respect to the horizontal plane. The term "couple" as in coupling or coupled means physical contact between elements whether direct or indirect.

Referring now to FIG. 1, therein is shown a front isometric view of the photography system 100 in a first embodiment. The photography system 100 is shown having a chassis 102.

The chassis 102 can include a chassis base 104 spanning horizontally between two vertical chassis extensions 106.

The chassis base 104 can include a frame mount 110. The frame mount 110 can be a mount configured for compatibility with a tripod, monopod, or gimbal for more stable video quality. It is further contemplated that some users may optionally mount a pistol grip to the frame mount 110.

The vertical chassis extensions 106 can extend upward from the chassis base 104. The vertical chassis extensions 106 can include chassis rails 112. The chassis rails 112 can enable the chassis 102 to be connected to device clamps 114 through the mating of device clamp rails 116 with the chassis rails 112.

The chassis rails 112 can further enable the chassis 102 to be connected to external mounts 118 through the mating of external mount rails 120 and the chassis rails 112. It is contemplated that the device clamps 114 and the external mounts 118 can be moveably coupled to the chassis 102.

The device clamps 114 can be adjusted vertically with respect to the chassis 102. The device clamp rails 116, being male, can be mated with the female chassis rails 112 for providing adjustable clamping for an imaging device 122.

The imaging device 122 can be a smart phone of various available widths and thicknesses. The device clamps 114 can include a tightening extension 124 coupled to a top clasp 126, a bottom clasp (shown in FIG. 2), and a screw 130.

The tightening extension 124 can be a thumbwheel or a set of tightening wheels used to tighten the device clamps 114 onto the imaging device 122. The tightening extension 124 is shown extended above the imaging device 122 for top access and ease of use. The top clasp 126 and the bottom clasp can both have the device clamp rails 116 formed thereon and can thereby mate with the chassis rails 112 for vertical movement.

The screw 130 can extend through the tightening extension 124, the top clasp 126, and the bottom clasp. Tightening the screw 130 by twisting the tightening extension 124 can force the top clasp 126 toward the bottom clasp to secure the imaging device 122.

Alternatively, it is contemplated that the screw 130 can be tightened into the chassis 102 by twisting the tightening extension 124. Tightening the screw 130 would also bring the top clasp 126 toward the bottom clasp as well as the chassis base 104 to secure the imaging device 122.

It is contemplated that the screw 130 may be left loose by a few millimeters. The tightening extension 124 can still be used to tighten the top clasp 126 as long as the screw 130 is engaged into the chassis 102. The tightening extension 124 may be loosened quickly yet, the head of the screw 130 can be retained within the tightening extension 124 without falling out.

In this way the head of the screw 130 can become a preset point from which to begin retightening the tightening extension 124. A properly set screw 130 would allow very fast removal and reattachment of the screw 130, because the minimum travel of the tightening extension 124 to allow imaging device 122 removal would be stored in the position of the screw 130.

The external mounts 118 can allow users to attach an external equipment 132. Illustratively, for example, the external mounts 118 can allow a user to mount an external microphone to be used with the imaging device 122 as is shown.

It is alternatively contemplated that the external mounts 118 can be used to secure larger, more powerful LED panels to the chassis 102. It is contemplated that the external mounts 118 can implement a hot shoe mount, which can allow mounting of many various external equipment. The tightening extension 124 can be located above the imaging device 122 and can be tightened down onto the imaging device 122.

The imaging device 122 can be positioned and affixed using the device clamps 114. The camera of the imaging device 122 can be positioned between the vertical chassis extensions 106 and can acquire images through the vertical chassis extensions 106.

To each of the vertical chassis extensions 106, light panels 134 and diffusion panels 136 can be mounted. As is shown, one of the light panels 134 and one of the diffusion panels 136 are affixed to each of the vertical chassis extensions 106.

The light panels 134 can be affixed to the vertical chassis extensions 106 with light panel attachments 138 while the diffusion panels 136 can be affixed to the vertical chassis extensions 106 with diffusion panel attachments 140. The light panels 134 can be battery powered LED panels used for illumination of dental and closeup photographs.

The light panels 134 can be rotationally oriented at 180 degrees from each other so their power switches (not pictured) are both on a single side such as on a top side. The diffusion panels 136 can be a translucent white acrylic diffusion panel for example.

It has been discovered that implementing the photography system 100 as described can provide cross lighting to teeth with a heavily diffused light. As will be appreciated this gives a glossy, yet textured look to the enamel.

That is, the light panels 134, the diffusion panels 136 and the imaging device 122 coupled together as shown and described can light teeth bilaterally with significant diffusion of the light. This creates uniform, soft lighting approximating the appearance of much larger, much more expensive studio lighting.

Figure 2:
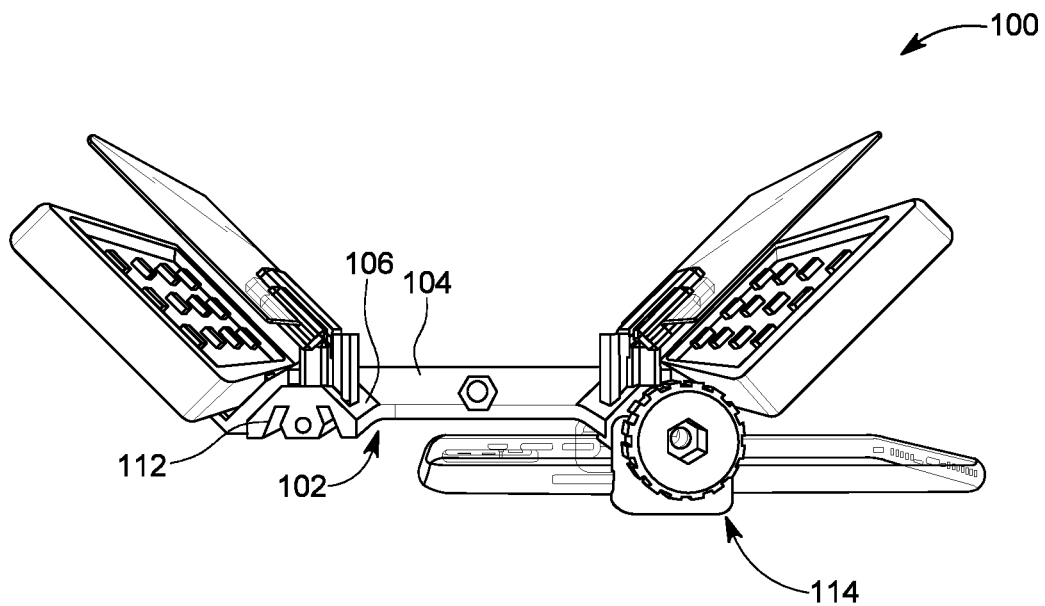
FIG. 2 is a top isometric view of the photography system of FIG. 1.

Referring now to FIG. 2, therein is shown a top isometric view of the photography system 100 of FIG. 1. The photography system 100 is shown with the chassis 102 with the vertical chassis extensions 106 extending up away from the chassis base 104.

The chassis rails 112 are depicted and shown formed within one of the vertical chassis extensions 106. It will be appreciated that the vertical chassis extensions 106 having the device clamps 114 also includes the chassis rails 112 mated to the device clamp rails 116 of FIG. 1 for the device clamps 114.

Figure 3:
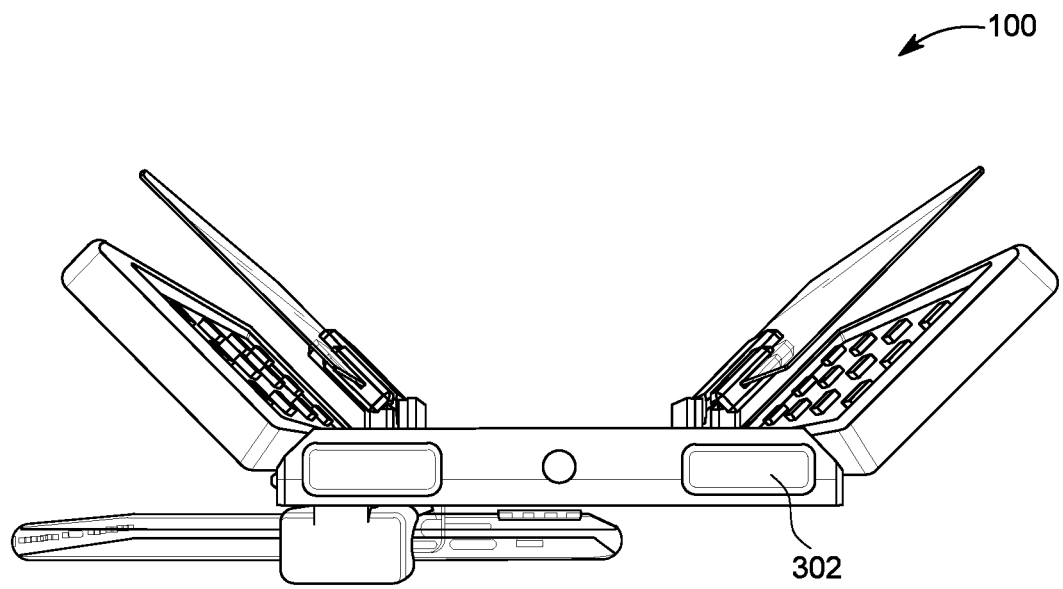
FIG. 3 is a bottom isometric view of the photography system of FIG. 1.

Referring now to FIG. 3, therein is shown a bottom isometric view of the photography system 100 of FIG. 1. The photography system 100 is shown having depressions 302. The depressions 302 can provide a thumb rest for the user to increase both comfort and to provide a more secure purchase on the photography system 100.

Figure 4:
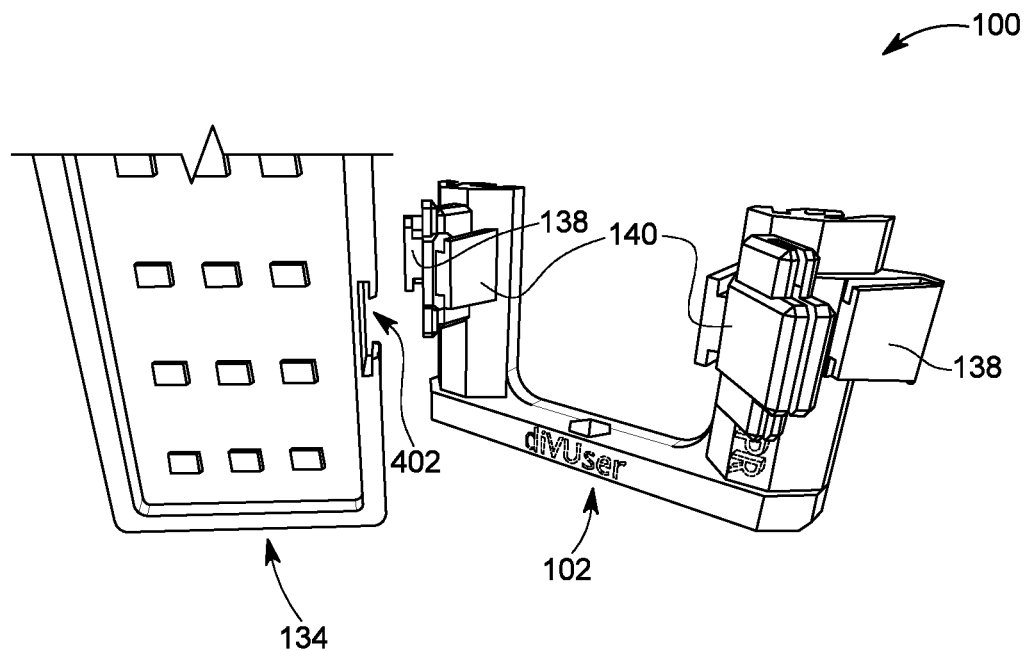
FIG. 4 is a front isometric view of the photography system of FIG. 1 in an attachment phase of operation.

Referring now to FIG. 4, therein is shown a front isometric view of the photography system 100 of FIG. 1 in an attachment phase of operation. The photography system 100 is shown having the chassis 102 adjacent to the light panels 134.

The chassis 102 is shown having the light panel attachments 138 along with the diffusion panel attachments 140. The light panel attachments 138 can be a tapered plane of plastic providing a friction fit between the light panel attachments 138 and a receiving recess 402 within the light panels 134.

The light panel attachments 138 can retain the light panels 134 to the chassis 102. The light panel attachments 138 can be a friction fit wedge and can be pushed into the receiving recess 402 of the light panels 134, the light panels 134 are tightened against the widening taper of the light panel attachments 138.

Again, the light panel attachments 138 is shown to gradually widen towards its posterior, providing a tighter fit as the light panels 134 are pressed onto the light panel attachments 138. It is contemplated that the light panel attachments 138 is over widened to allow for more retention as the plastic wears over time.

The diffusion panel attachments 140 can also be seen as a friction fit clamp for holding the diffusion panels 136 of FIG. 1. As the diffusion panels 136 are pushed into the diffusion panel attachments 140 the diffusion panels 136 are held ever more securely.

Figure 5:
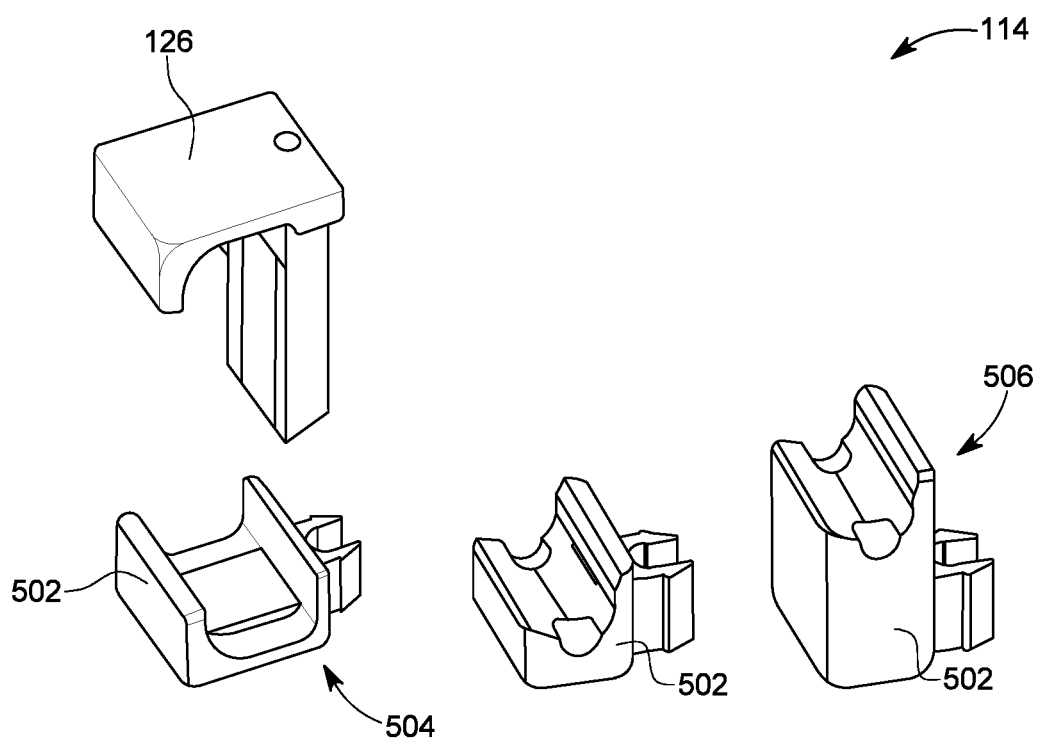
FIG. 5 is an isometric view of the device clamps of FIG. 1.

Referring now to FIG. 5, therein is shown an isometric view of the device clamps 114 of FIG. 1. Portions of the device clamps 114 are shown, specifically the top clasp 126 and bottom clasps 502 are shown.

As will be appreciated, the top clasp 126 and the bottom clasp 502 are shown with a widened cross section 504 to support larger imaging devices 122 of FIG. 1 or imaging devices 122 having extended battery attachments.

The top clasp 126 and the bottom clasp 502 can also have a thicker cross section 506 to support narrow or slim imaging devices 122. It is alternatively contemplated that when the imaging device 122 is used on the opposite side, or left side, of the chassis 102 of FIG. 1 the bottom clasp 502 having the thicker cross section 506 can be used to lift the camera lens upward, above the chassis base 104 of FIG. 1 when clamped down.

The bottom clasps 502 and the top clasps 126 are shown having cutouts 508. The cutouts 508 can prevent the buttons on the imaging device 122 from being depressed when the imaging device 122 is clamped down. This allows more latitude in imaging device 122. It is contemplated that the various structural layouts of the top clasp 126 and the bottom clasp 502 will accommodate all major imaging devices 122, even if they have thick cases.

The bottom clasps 502 are depicted having mounting clips 510. The mounting clips 510 can have a hollow center for allowing the screw 130 of FIG. 1 to pass therethrough.

Figure 6:
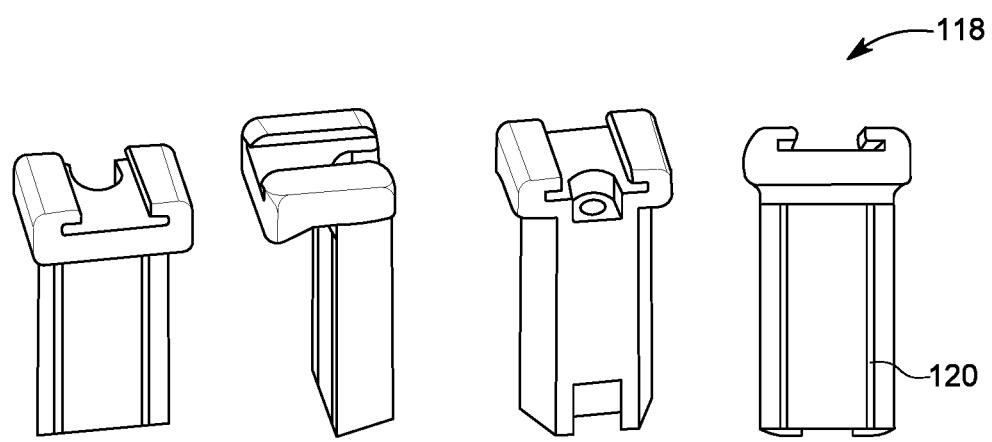
FIG. 6 is an isometric view of the external mounts of FIG. 1.

Referring now to FIG. 6, therein is shown an isometric view of the external mounts 118 of FIG. 1. The external mounts 118 are shown having the external mount rails 120 formed therein.

The external mounts 118 can be configured with a hot shoe attachment. The hot shoe attachment is compatible with a wide variety of videography and photography accessories, such as external microphones, lighting devices, flashes, and others.

Figure 7:
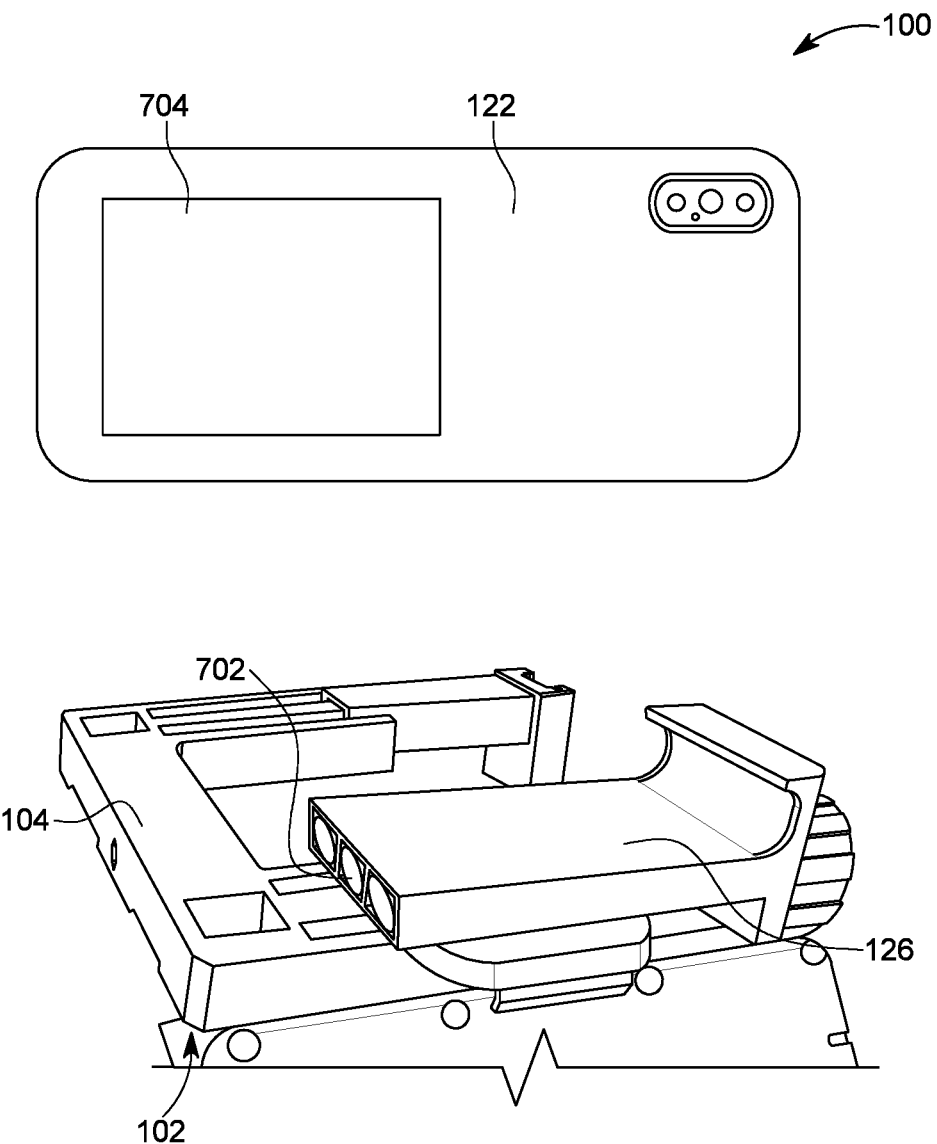
FIG. 7 is a back isometric view of the photography system of FIG. 1.

Referring now to FIG. 7, therein is shown a back isometric view of the photography system 100 of FIG. 1. The photography system 100 is shown with the top clasp 126 having magnets 702.

The magnets 702 are depicted on the top clasp 126 near the chassis base 104. It is contemplated that each of the top clasps 126 can include the magnets 702 whether exposed from a side of the top clasp 126, as shown in FIG. 7, or fully enclosed within the top clasps 126.

The magnets 702 can be aligned with a magnetic adhesive 704 adhered to the imaging device 122. The magnetic adhesive 704 can be a metallic or magnetic disc or adhesive that can be installed on the imaging device 122.

It has been discovered that the inclusion of the magnets 702 together with the magnetic adhesive 704 can rigidly hold the imaging device 122 to the top clasp 126. Further, the magnetic adhesive 704 together with the magnets 702 can enable immediate alignment between the imaging device 122 and the chassis 102.

Figure 8:
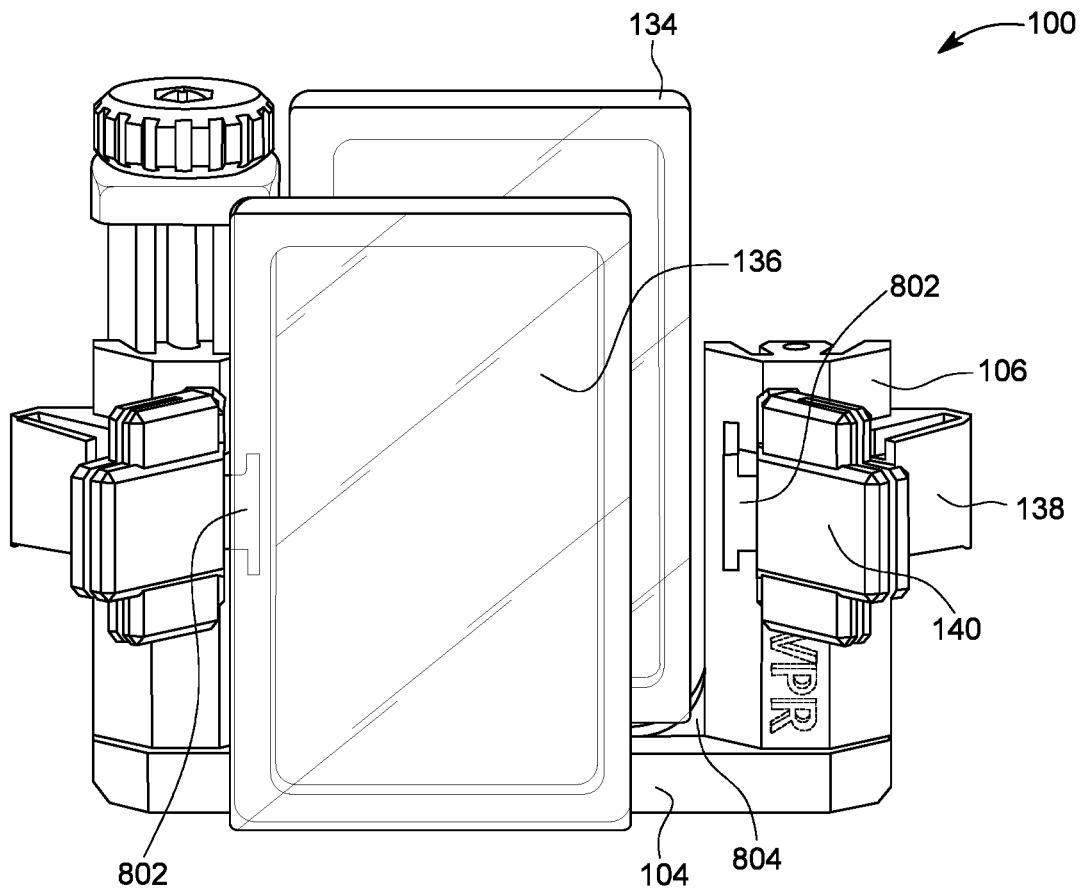
FIG. 8 is a front isometric view of the photography system of FIG. 1 in a closed configuration.

Referring now to FIG. 8, therein is shown a front isometric view of the photography system 100 of FIG. 1 in a closed configuration. The light panels 134 and the diffusion panels 136 can be stored and positioned on the chassis base 104 between the vertical chassis extensions 106.

The light panel 134 and the diffusion panel 136 between the vertical chassis extensions 106 can be detached from the light panel attachments 138 and the diffusion panel attachments 140, respectively.

One of the light panels 134 can be attached to storage attachments 802 on both of the vertical chassis extensions 106. The storage attachments 802 can be similar in form and function to the light panel attachments 138 of FIG. 1 described above.

However, the position of the storage attachments 802 enables one of the light panels 134 and the diffusion panels 136 to be stored and secured between the vertical chassis extensions 106 and the other of the two light panels 134, which is coupled to the storage attachments 802. The light panel 134 and the diffusion panels 136 can rest on the vertical chassis extensions 106 and a storage back 804.

Figure 9:
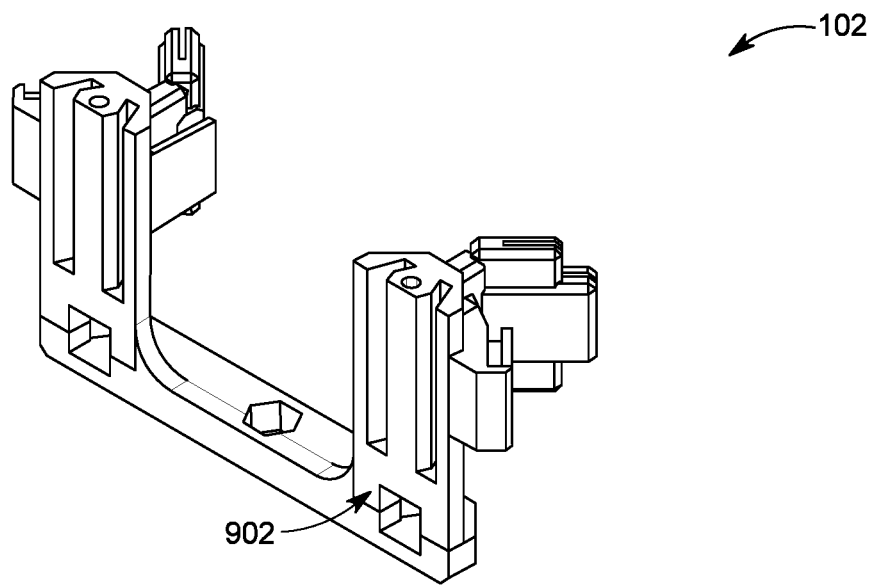
FIG. 9 is a back isometric view of the chassis of FIG. 1.

Referring now to FIG. 9, therein is shown a back isometric view of the chassis 102 of FIG. 1. The chassis 102 is shown to be symmetrical about a vertical axis. This can allow the imaging device 122 of FIG. 1 to be used on either the left or right side. Similarly, the external mounts 118 of FIG. 1 can be used and mounted on either the right or left side.

The chassis 102 is shown having mounting recesses 902 for receiving the mounting clips 510 of FIG. 5 of the bottom clasps 502 of FIG. 5. When configured to use the mounting recesses 902 with the mounting clips 510, the bottom clasps 502 will be stationary with respect to the chassis 102 unlike the top clasp 126 of FIG. 1 which would be vertically moveable.

Figure 10:
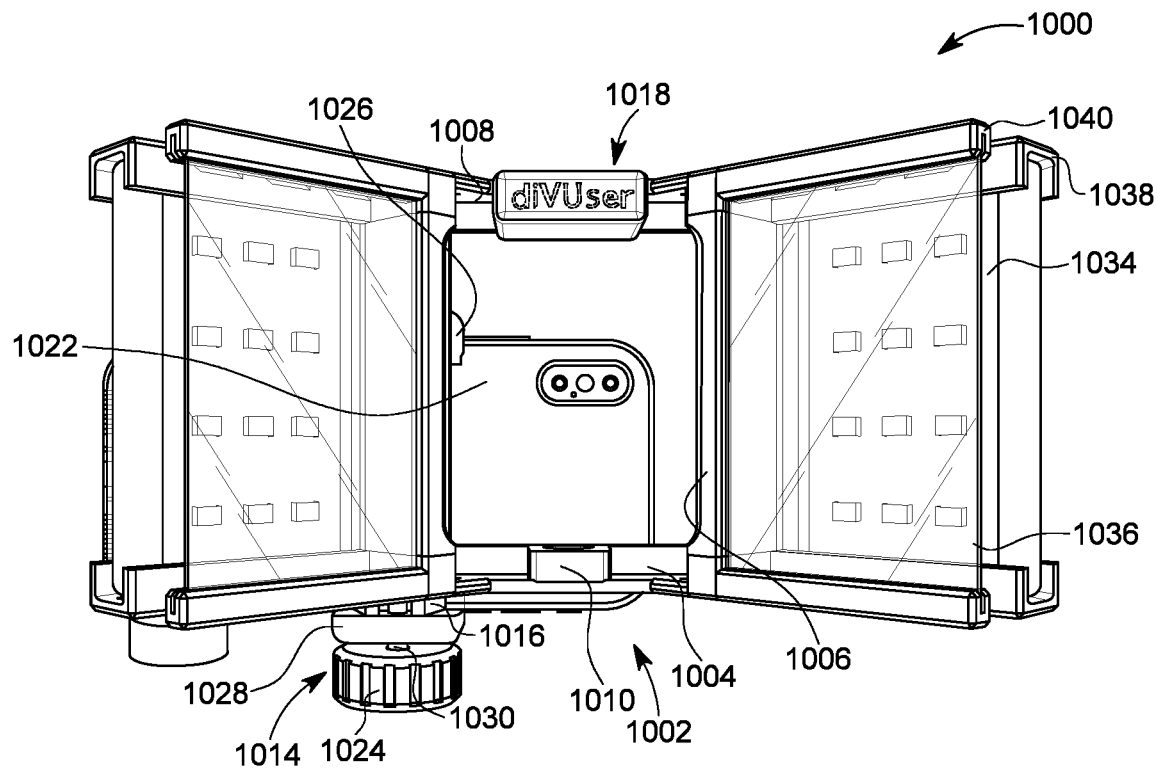
FIG. 10 is a front isometric view of the photography system in a second embodiment.

Referring now to FIG. 10, therein is shown a front isometric view of the photography system 1000 in a second embodiment. The photography system 1000 is shown having a chassis 1002.

The chassis 1002 can include a chassis base 1004 spanning horizontally between two vertical chassis extensions 1006.

The chassis base 1004 can include a frame mount 1010. The frame mount 1010 can be a mount configured for compatibility with a tripod, monopod, or gimbal for more stable video quality. It is further contemplated that some users may optionally mount a pistol grip to the frame mount 1010.

The vertical chassis extensions 1006 can extend upward from the chassis base 1004. The vertical chassis extensions 1006 can include chassis rails similar to the chassis rails 112 of FIG. 1. The chassis rails can enable the chassis 1002 to be connected to device clamps 1014 through the mating of device clamp rails 1016 with the chassis rails. It is contemplated that the device clamps 1014 can be moveably coupled to the chassis 1002.

The vertical chassis extensions 1006 can further enable the chassis 1002 to be connected to and incorporate external mounts 1018. The external mounts 1018 can be seen spanning between the vertical chassis extensions 1006.

The device clamps 1014 can be adjusted vertically with respect to the chassis 1002. The device clamp rails 1016, being male, can be mated with the female chassis rails for providing adjustable clamping for an imaging device 1022.

The imaging device 1022 can be a smart phone of various available widths and thicknesses. The device clamps 1014 can include a tightening extension 1024 coupled to a top clasp 1026, a bottom clasp 1028, and a screw 1030.

The tightening extension 1024 can be a thumbwheel or a set of tightening wheels used to tighten the device clamps 1014 onto the imaging device 1022. The tightening extension 1024 is shown extended below the imaging device 122 for bottom access and ease of use. The top clasp 1026 and the bottom clasp 1028 can both have the device clamp rails 1016 formed thereon and can thereby mate with the chassis rails for vertical movement.

The screw 1030 can extend through the tightening extension 1024, the top clasp 1026, and the bottom clasp 1028. Tightening the screw 1030 by twisting the tightening extension 1024 can force the top clasp 1026 toward the bottom clasp to secure the imaging device 1022.

Alternatively, it is contemplated that the screw 1030 can be tightened into the chassis 1002 by twisting the tightening extension 1024. Tightening the screw 1030 would also bring the top clasp 1026 toward the bottom clasp as well as the chassis base 1004 to secure the imaging device 1022.

It is contemplated that the screw 1030 may be left loose by a few millimeters. The tightening extension 1024 can still be used to tighten the top clasp 1026 as long as the screw 1030 is engaged into the chassis 1002. The tightening extension 1024 may be loosened quickly yet, the head of the screw 1030 can be retained within the tightening extension 1024 without falling out.

In this way the head of the screw 1030 can become a preset point from which to begin retightening the tightening extension 1024. A properly set screw 1030 would allow very fast removal and reattachment of the screw 1030, because the minimum travel of the tightening extension 1024 to allow imaging device 1022 removal would be stored in the position of the screw 1030.

The external mounts 1018 can allow users to attach an external equipment. Illustratively, for example, the external mounts 1018 can allow a user to mount an external microphone to be used with the imaging device 1022.

It is alternatively contemplated that the external mounts 1018 can be used to secure larger, more powerful LED panels to the chassis 1002. It is contemplated that the external mounts 1018 can implement a hot shoe mount, which can allow mounting of many various external equipment. The tightening extension 1024 can be located above the imaging device 1022 and can be tightened down onto the imaging device 1022.

The imaging device 1022 can be positioned and affixed using the device clamps 1014. The camera of the imaging device 1022 can be positioned between the vertical chassis extensions 1006 and can acquire images through the vertical chassis extensions 1006.

To each of the vertical chassis extensions 1006, light panels 1034 and diffusion panels 1036 can be mounted. As is shown, one of the light panels 1034 and one of the diffusion panels 1036 are affixed to each of the vertical chassis extensions 1006.

The light panels 1034 can be affixed to the vertical chassis extensions 1006 with light panel attachments 1038 while the diffusion panels 1036 can be affixed to the vertical chassis extensions 1006 with diffusion panel attachments 1040. The light panel attachments 1038 can be a slot providing a friction fit.

That is the light panels 1034 can be slid into a slightly tapered slot, which comprises the light panel attachments 1038. The light panels 1034 are then held securely within the light panel attachments 1038 allowing the molding system 1000 to be manipulated without risk of the light panels 1034 becoming detached from the chassis 1002.

The light panels 1034 can be battery powered LED panels used for illumination of dental and closeup photographs. The light panels 1034 can be rotationally oriented at 180 degrees from each other so their power switches (not pictured) are both on a single side such as on a top side.

The diffusion panels 1036 can be a translucent white acrylic diffusion panel for example. The diffusion panel attachments 1040 can be a slot providing a friction fit.

That is the diffusion panels 1036 can be slid into a slightly tapered slot, which comprises the diffusion panel attachments 1040. The diffusion panels 1036 are then held securely within the diffusion panel attachments 1040 allowing the molding system 1000 to be manipulated without risk of the diffusion panels 1036 becoming detached from the chassis 1002.

It has been discovered that implementing the photography system 1000 as described can provide cross lighting to teeth with a heavily diffused light. As will be appreciated this gives a glossy, yet textured look to the enamel.

That is, the light panels 1034, the diffusion panels 1036 and the imaging device 1022 coupled together as shown and described can light teeth bilaterally with significant diffusion of the light. This creates uniform, soft lighting approximating the appearance of much larger, much more expensive studio lighting.

The diffusion panel attachments 1040 together with the light panel attachments 1038 can have a fixed mounting position with respect to the imaging device 1022 and with respect to the chassis 1002. The fixed mounting position creates consistently soft light, which improves the highlights on the teeth, and significantly minimizes eye strain to the patient.

The fixed mounting of the light panels 1034 can have a fixed angle of 45 degrees off the chassis 1002, or 135 degrees spanning between the light panels 1034. This has been discovered to provide a predictable lighting result for a given distance. It also allows for a variation of lighting effect by altering distance from light source to subject. Other units can vary angles, but a fixed lighting angle allows for greater consistency and structural rigidity.

Figure 11:
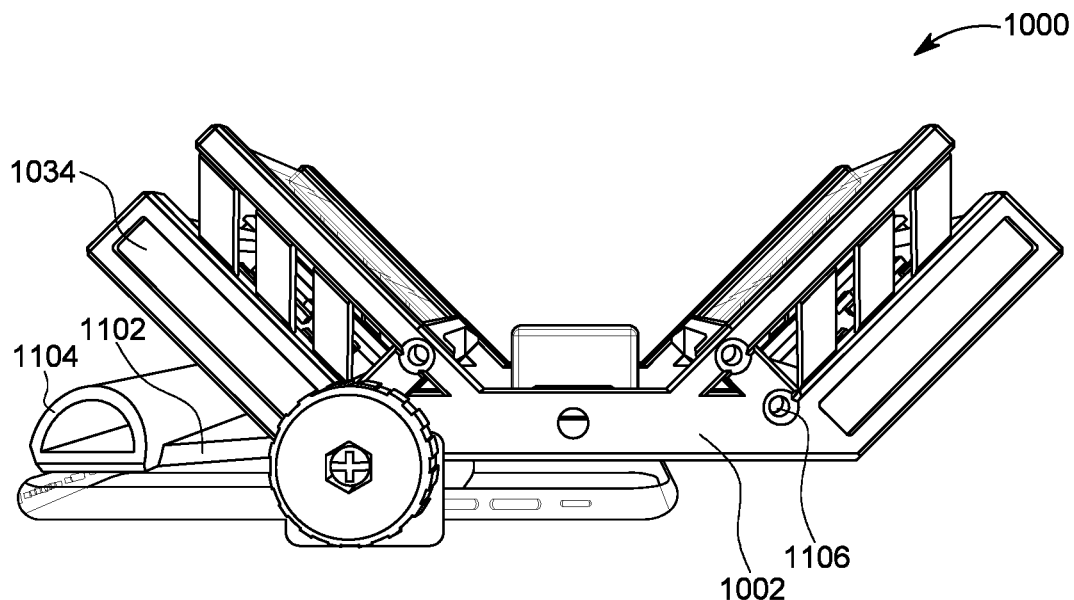
FIG. 11 is a bottom isometric view of the photography system of FIG. 10.

Referring now to FIG. 11, therein is shown a bottom isometric view of the photography system 1000 of FIG. 10. The photography system 1000 is shown having a grip bar 1102 with a handle 1104.

The grip bar 1102 can allow a user to operate the photography system 1000 with a single hand, with fingers sandwiched between the grip 1104 and the bottom surface of the right light panel 1034. A cutout 1106 in the chassis 1002 can allow a charging cable for the light panels 1034 to passthrough. This can enable the light panels 1034 to be charged without removing the light panels 1034 from the chassis 1002.

Figure 12:
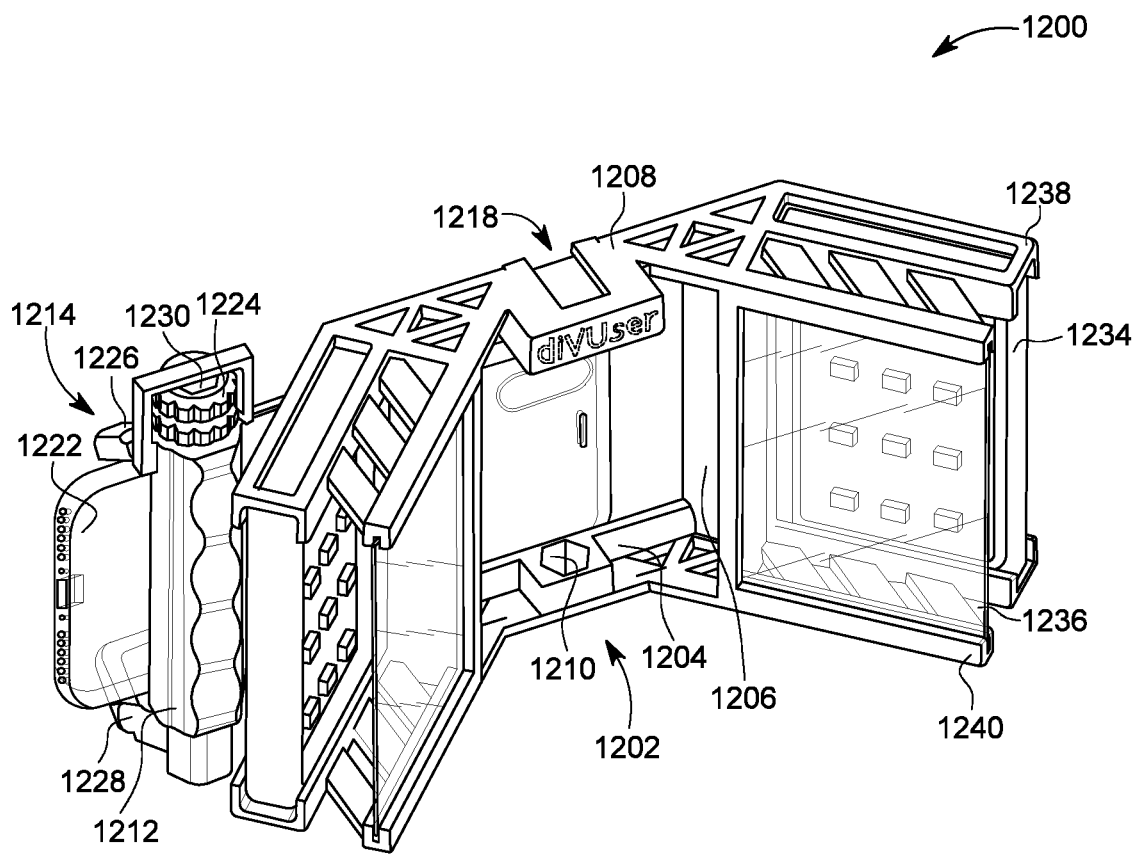
FIG. 12 is a top front isometric view of the photography system in a third embodiment.

Referring now to FIG. 12, therein is shown a top front isometric view of the photography system 1200 in a third embodiment. The photography system 1200 is shown having a chassis 1202.

The chassis 1202 can include a chassis base 1204 spanning horizontally between two vertical chassis extensions 1206.

The chassis base 1204 can include a frame mount 1210. The frame mount 1210 can be a mount configured for compatibility with a tripod, monopod, or gimbal for more stable video quality. It is further contemplated that some users may optionally mount a pistol grip to the frame mount 1210.

The vertical chassis extensions 1206 can extend upward from the chassis base 1204. The vertical chassis extensions 1206 can include chassis rails similar to the chassis rails 112 of FIG. 1 within a handle 1212 extended horizontally away from one of the vertical chassis extensions 1206.

As is illustratively depicted, the outer surface of the vise clamp also doubles the handle 1212 to hold the photography system 1200 like a traditional camera. When using this grasp, the shutter buttons on most phone apps are accessible with the user's right thumb. This has been discovered to provide intuitive and effective one handed operation. It will be appreciated that the photography system 1200 can allow a user to operate the smartphone with the right hand, while positioning a mirror or retractor with the other hand. The entire rig may be inverted to use with the left hand. It is contemplated that all current smartphones will orient their apps and their images to compensate.

The chassis rails can enable the chassis 1202 to be connected to device clamps 1214 through the mating of device clamp rails, similar to the device clamp rails 116 of FIG. 1, with the chassis rails. It is contemplated that the device clamps 1214 can be moveably coupled to the chassis 1202.

The vertical chassis extensions 1206 can further enable the chassis 1202 to be connected to and incorporate external mounts 1218. The external mounts 1218 can be seen spanning between the vertical chassis extensions 1206.

The device clamps 1214 can be adjusted vertically with respect to the chassis 1202. The device clamp rails can be male and can be mated with the female chassis rails for providing adjustable clamping for an imaging device 1222.

The imaging device 1222 can be a smart phone of various available widths and thicknesses. The device clamps 1214 can include a tightening extension 1224 coupled to a top clasp 1226, a bottom clasp 1228, and a screw 1230.

The tightening extension 1224 can be a thumbwheel or a set of tightening wheels used to tighten the device clamps 1214 onto the imaging device 1222. The tightening extension 1224 is shown extended above the imaging device 1222 for top access and ease of use. The top clasp 1226 and the bottom clasp 1228 can both have the device clamp rails formed thereon and can thereby mate with the chassis rails for vertical movement.

The screw 1230 can extend through the tightening extension 1224, the top clasp 1226, and the bottom clasp 1228. Tightening the screw 1230 by twisting the tightening extension 1224 can force the top clasp 1226 toward the bottom clasp to secure the imaging device 1222. When multiple tightening wheels are used, the tightening wheels can lock the imaging device 1222.

Alternatively, it is contemplated that the screw 1230 can be tightened into the chassis 1202 by twisting the tightening extension 1224. Tightening the screw 1230 would also bring the top clasp 1226 toward the bottom clasp as well as the chassis base 1204 to secure the imaging device 1222.

It is contemplated that the screw 1230 may be left loose by a few millimeters. The tightening extension 1224 can still be used to tighten the top clasp 1226 as long as the screw 1230 is engaged into the chassis 1202. The tightening extension 1224 may be loosened quickly yet, the head of the screw 1230 can be retained within the tightening extension 1224 without falling out.

In this way the head of the screw 1230 can become a preset point from which to begin retightening the tightening extension 1224. A properly set screw 1230 would allow very fast removal and reattachment of the screw 1230, because the minimum travel of the tightening extension 1224 to allow imaging device 1222 removal would be stored in the position of the screw 1230.

The external mounts 1218 can allow users to attach an external equipment. Illustratively, for example, the external mounts 1218 can allow a user to mount an external microphone to be used with the imaging device 1222.

It is alternatively contemplated that the external mounts 1218 can be used to secure larger, more powerful LED panels to the chassis 1202. It is contemplated that the external mounts 1218 can implement a hot shoe mount, which can allow mounting of many various external equipment. The tightening extension 1224 can be located above the imaging device 1222 and can be tightened down onto the imaging device 1222.

The imaging device 1222 can be positioned and affixed using the device clamps 1214. The camera of the imaging device 1222 can be positioned between the vertical chassis extensions 1206 and can acquire images through the vertical chassis extensions 1206.

To each of the vertical chassis extensions 1206, light panels 1234 and diffusion panels 1236 can be mounted. As is shown, one of the light panels 1234 and one of the diffusion panels 1236 are affixed to each of the vertical chassis extensions 1206.

The light panels 1234 can be affixed to the vertical chassis extensions 1206 with light panel attachments 1238 while the diffusion panels 1236 can be affixed to the vertical chassis extensions 1206 with diffusion panel attachments 1240. The light panel attachments 1238 can be a slot providing a friction fit.

That is the light panels 1234 can be slid into a slightly tapered slot, which comprises the light panel attachments 1238. The light panels 1234 are then held securely within the light panel attachments 1238 allowing the molding system 1200 to be manipulated without risk of the light panels 1234 becoming detached from the chassis 1202.

The light panels 1234 can be battery powered LED panels used for illumination of dental and closeup photographs. The light panels 1234 can be rotationally oriented at 180 degrees from each other so their power switches (not pictured) are both on a single side such as on a top side. Further, as is shown, cutouts and holes in the chassis 1202 can allow a USB cable of the light panels 1234 to passthrough. This allows charging of the light panels 1234 without removing it from the chassis.

The diffusion panels 1236 can be a translucent white acrylic diffusion panel for example. The diffusion panel attachments 1240 can be a slot providing a friction fit.

That is the diffusion panels 1236 can be slid into a slightly tapered slot, which comprises the diffusion panel attachments 1240. The diffusion panels 1236 are then held securely within the diffusion panel attachments 1240 allowing the molding system 1200 to be manipulated without risk of the diffusion panels 1236 becoming detached from the chassis 1202.

It has been discovered that implementing the photography system 1200 as described can provide cross lighting to teeth with a heavily diffused light. As will be appreciated this gives a glossy, yet textured look to the enamel.

That is, the light panels 1234, the diffusion panels 1236 and the imaging device 1222 coupled together as shown and described can light teeth bilaterally with significant diffusion of the light. This creates uniform, soft lighting approximating the appearance of much larger, much more expensive studio lighting.

The diffusion panel attachments 1240 together with the light panel attachments 1238 can have a fixed mounting position with respect to the imaging device 1222 and with respect to the chassis 1202. The fixed mounting position creates consistently soft light, which improves the highlights on the teeth, and significantly minimizes eye strain to the patient.

The fixed mounting of the light panels 1234 can have a fixed angle of 45 degrees off the chassis 1202, or 135 degrees spanning between the light panels 1234. This has been discovered to provide a predictable lighting result for a given distance. It also allows for a variation of lighting effect by altering distance from light source to subject. Other units can vary angles, but a fixed lighting angle allows for greater consistency and structural rigidity.

Figure 13:
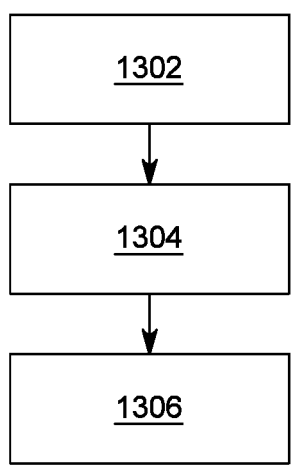
FIG. 13 is a flow chart for manufacturing the oral photography system.

Referring now to FIG. 13, therein is shown a flow chart for manufacturing the oral photography system. The method includes: providing a chassis, the chassis including a chassis base and a vertical chassis extension, the vertical chassis extension extending upward from the chassis base, the vertical chassis extension including a device clamp having a tightening extension coupled to a top clasp and a bottom clasp, the top clasp and the bottom clasp configured to hold an imaging device perpendicular to the vertical chassis extension, a diffusion panel attachment coupled to the vertical chassis extension, and a light panel attachment coupled to the vertical chassis extension in a block 1302; attaching a diffusion panel releasably affixed to the diffusion panel attachment in a block 1304; and attaching a light panel releasably affixed to the light panel attachment in a block 1306.

Thus, it has been discovered that the photography system furnishes important and heretofore unknown and unavailable solutions, capabilities, and functional aspects. The resulting configurations are straightforward, cost-effective, uncomplicated, highly versatile, accurate, sensitive, and effective, and can be implemented by adapting known components for ready, efficient, and economical manufacturing, application, and utilization.

While the photography system has been described in conjunction with a specific best mode, it is to be understood that many alternatives, modifications, and variations will be apparent to those skilled in the art in light of the preceding description. Accordingly, it is intended to embrace all such alternatives, modifications, and variations, which fall within the scope of the included claims. All matters set forth herein or shown in the accompanying drawings are to be interpreted in an illustrative and non-limiting sense.

What is claimed is:

1. An oral photography system comprising:
 a chassis, the chassis including a chassis base and a vertical chassis extension, the vertical chassis extension extending upward from the chassis base, and the vertical chassis extension including:
   a device clamp having a tightening extension coupled to a top clasp and a bottom clasp, the top clasp and the bottom clasp configured to hold an imaging device perpendicular to the vertical chassis extension,
   a diffusion panel attachment coupled to the vertical chassis extension, and
   a light panel attachment coupled to the vertical chassis extension;
 a diffusion panel releasably affixed to the diffusion panel attachment; and
 a light panel releasably affixed to the light panel attachment.

2. The system of claim 1 wherein the chassis base includes a frame mount for mounting the chassis base to a tripod.

3. The system of claim 1 wherein the vertical chassis extension includes fame rails therein, and the device clamps are moveably coupled to the vertical chassis extension with the frame rails.

4. The system of claim 1 wherein the light panel attachment is a slightly tapered slot or a friction fit wedge.

5. The system of claim 1 wherein the top clasp, the bottom clasp, or a combination thereof include cutouts for preventing buttons on the imaging device from being depressed.

6. An oral photography system comprising:
 a chassis, the chassis including a chassis base and vertical chassis extensions, the vertical chassis extensions extending upward from the chassis base, the chassis base spanning horizontally between the vertical chassis extensions, and at least one of the vertical chassis extensions including:
   a device clamp having a tightening extension coupled to a top clasp having a magnet therein, and the tightening extension coupled to a bottom clasp, the top clasp and the bottom clasp configured to hold an imaging device perpendicular to the vertical chassis extensions, the imaging device having a magnetic adhesive for magnetically coupling with the magnet within the top clasp for rigidly holding the imaging device to the top clasp,
   a diffusion panel attachment coupled to the at least one of the vertical chassis extensions, and
   a light panel attachment coupled to the at least one of the vertical chassis extensions;
 a diffusion panel releasably affixed to the diffusion panel attachment; and
 a light panel releasably affixed to the light panel attachment.

7. The system of claim 6 further comprising an external mount coupled to one of the vertical chassis extensions.

8. The system of claim 7 wherein the external mount is a hot shoe mount.

9. The system of claim 6 wherein the imaging device is a digital phone.

10. The system of claim 6 wherein the vertical chassis extensions include storage attachments for storing the light panel between the vertical chassis extensions.

11. A method of manufacturing an oral photography system comprising:
 providing a chassis, the chassis including a chassis base and a vertical chassis extension, the vertical chassis extension extending upward from the chassis base, the vertical chassis extension including:
   a device clamp having a tightening extension coupled to a top clasp and a bottom clasp, the top clasp and the bottom clasp configured to hold an imaging device perpendicular to the vertical chassis extension,
   a diffusion panel attachment coupled to the vertical chassis extension, and
   a light panel attachment coupled to the vertical chassis extension;

attaching a diffusion panel releasably affixed to the diffusion panel attachment; and attaching a light panel releasably affixed to the light panel attachment.

12. The method of claim 11 wherein providing the chassis includes providing the chassis including the chassis base having a frame mount for mounting the chassis base to a tripod.

13. The method of claim 11 wherein providing the chassis includes providing the chassis including the vertical chassis extension having fame rails therein, and the device clamps are moveably coupled to the vertical chassis extension with the frame rails.

14. The method of claim 11 wherein providing the chassis includes providing the chassis including the light panel attachment being a slightly tapered slot or a friction fit wedge.

15. The method of claim 11 wherein providing the chassis includes providing the chassis including the top clasp, the bottom clasp, or a combination thereof having cutouts for preventing buttons on the imaging device from being depressed.

16. The method of claim 11 wherein providing the chassis includes providing the chassis with the vertical chassis extension being one of two vertical chassis extensions, the vertical chassis extensions extending upward from the chassis base, and the chassis base spanning horizontally between the vertical chassis extensions, and at least one of the vertical chassis extensions including the device clamp having a magnet therein, and the imaging device having a magnetic adhesive for magnetically coupling with the magnet within the top clasp for rigidly holding the imaging device to the top clasp.

17. The method of claim 16 further comprising attaching an external mount to one of the vertical chassis extensions.

18. The method of claim 17 wherein attaching the external mount includes attaching a hot shoe mount.

19. The method of claim 16 wherein providing the chassis includes providing the chassis including the top clasp and the bottom clasp configured to hold a digital phone.

20. The method of claim 16 wherein providing the chassis includes providing the chassis including the vertical chassis extensions having storage attachments for storing the light panel between the vertical chassis extensions.

* * * * *